United States Patent [19]

Trampota et al.

[11] Patent Number: 5,618,959

[45] Date of Patent: Apr. 8, 1997

[54] PROCESS FOR PREPARING PROSTAGLANDIN E1, E2 AND ANALOGS THEREOF USING FURYLCOPPER REAGENTS

[75] Inventors: Miroslav Trampota, West Orange; Bohumil Zak, Mapplewood, both of N.J.

[73] Assignee: Vivus Incorporated, Menlo Park, Calif.

[21] Appl. No.: 403,251

[22] Filed: Mar. 10, 1995

[51] Int. Cl.$^6$ ........................................ C07F 7/18
[52] U.S. Cl. ........................ 556/437; 549/416; 549/422; 549/427; 549/505; 560/121; 560/122; 562/503; 562/504
[58] Field of Search ............................ 556/437; 549/416, 549/422, 427, 505; 560/121, 122; 562/503, 504

[56] References Cited

U.S. PATENT DOCUMENTS

| | | |
|---|---|---|
| 4,031,129 | 6/1977 | Sih . |
| 4,087,621 | 5/1978 | Collins et al. . |
| 4,088,536 | 5/1978 | Sih . |
| 4,149,007 | 4/1979 | Buckler et al. . |
| 4,282,372 | 8/1981 | Matsuo et al. . |
| 4,360,688 | 11/1982 | Floyd, Jr. . |
| 4,410,720 | 10/1983 | Holland et al. ............... 549/422 X |
| 4,452,994 | 6/1984 | Hill et al. . |
| 4,474,979 | 10/1984 | Floyd, Jr. . |
| 4,535,180 | 8/1985 | Grudzinskas et al. . |
| 4,543,421 | 9/1985 | Corey et al. . |
| 4,644,079 | 2/1987 | Floyd, Jr. et al. . |
| 4,785,124 | 11/1988 | Campbell et al. . |
| 4,904,820 | 2/1990 | Campbell et al. . |
| 4,952,710 | 8/1990 | Babiak et al. . |
| 4,983,753 | 1/1991 | Floyd, Jr. et al. . |
| 5,055,604 | 10/1991 | Babiak et al. . |
| 5,166,369 | 11/1992 | Floyd, Jr. et al. . |
| 5,191,109 | 3/1993 | Minai et al. . |

FOREIGN PATENT DOCUMENTS

| | | |
|---|---|---|
| A2385696 | 10/1978 | France . |
| A2401899 | 3/1979 | France . |
| 63-077837 | 4/1988 | Japan . |

OTHER PUBLICATIONS

Lipshutz, "Applications of Higher–Order Mixed Organocuprates to Organic Synthesis," *Synthesis* 4:325–341 (1987).
Chen et al., *J. Organic Chem.*, 43(18):3450–3454 (1978).
Lipshutz et al., *Tetrahedron Lett.*, 42(11):2873–2879 (1986).
Ng et al., *Tetrahedron Lett.*, 29(25):3045–3048 (1988).

*Primary Examiner*—Paul F. Shaver
*Attorney, Agent, or Firm*—Reed & Robins

[57] ABSTRACT

A process for synthesizing prostaglandin $E_1$, $E_2$ and derivatives thereof is provided. The process is a "one-pot" method in which 2-furyllithium, copper cyanide, a lower alkyllithium reagent and either an (E)-alkenylstannane or a halogenide are combined with cyclopentenone (II)

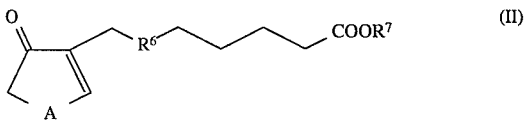

in which A, $R^6$ and $R^7$ are as defined herein. The reaction gives rise to the desired prostaglandin product in yields of 80% or higher.

27 Claims, No Drawings

PROCESS FOR PREPARING PROSTAGLANDIN E1, E2 AND ANALOGS THEREOF USING FURYLCOPPER REAGENTS

TECHNICAL FIELD

This invention relates generally to methods for synthesizing derivatives of prostanoic acid, and more particularly relates to a "one-pot" method for synthesizing prostaglandin $E_1$ ("$PGE_1$"), prostaglandin $E_2$ ("$PGE_2$") and derivatives thereof using furyl copper reagents.

BACKGROUND

Prostaglandins are a family of biologically active lipid acids that possess as a common feature the prostan-1-oic acid structure

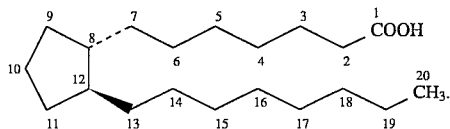

Prostaglandins are grouped into the types E, F, A, B, C and D, based on the presence or absence of certain functionalities in the cyclopentane ring. The numerical subscripts, as in, for example, prostaglandin "$E_1$" and prostaglandin "$E_2$," refer to the number of unsaturated bonds in the side chains; the subscripts "$\alpha$" or "$\beta$" as in prostaglandin "$F_{1\alpha}$" or prostaglandin "$F_{1\beta}$," refer to the configuration of substituents in the ring.

Biological activities of the prostaglandins include stimulation of smooth muscle, dilation of small arteries, bronchial dilation, lowering of blood pressure, inhibition of gastric secretion, lipolysis, and platelet aggregation, induction of labor, abortion, and menstruation, and increase in ocular pressure. $PGE_1$, specifically, is known as a bronchodilator and a vasodilator, and is also known to stimulate release of erythropoietin from the renal cortex and to inhibit allergic responses and blood-platelet aggregation. $PGE_2$, the most common and most biologically potent of the mammalian prostaglandins, acts to contract the uterine muscle, to inhibit gastric acid secretion and protect the gastric mucosal lining and, like $PGE_1$, has been established to be a bronchodilator and a stimulant of the release of erythropoietin from the renal cortex. Properties of the various prostaglandins have been reviewed extensively; see, e.g., Ramwell et al., *Nature* 221:1251 (1969).

Biosynthesis of the prostaglandins occurs by enzymatic conversion of unsaturated twenty-carbon fatty acids. For example, the endoperoxides $PGG_2$ and $PGH_2$ are prepared by the action of the enzyme complex prostaglandin cyclooxygenase on the lipid precursor arachidonic acid, while $PGE_1$ is biosynthesized by enzymatic conversion of 8,11,14-eicosatrienoic acid. Biosynthetic studies of the prostaglandins are reviewed in Samuelsson, *Prog. Biochem. Pharmacol.* 5:109 (1969).

A number of synthetic routes to the various prostaglandins have been explored. A twenty-step synthesis to $PGE_2$ and $PGF_{2\alpha}$, starting with thallous cyclopentadiene, was developed by Corey et al. The process has also proved to be useful in the synthesis of the one-series prostaglandins. Catalytic reduction of bis-protected $PGF2\alpha$ results in selective saturation of the 5,6-double bond to afford

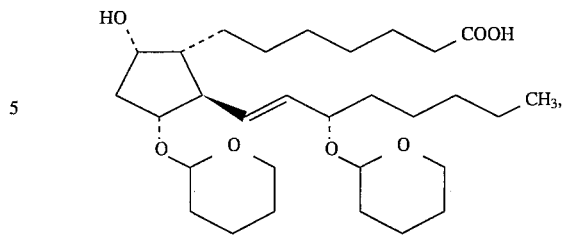

followed by transformations leading to $PGE_1$ and $PGF_{1\alpha}$. See, e.g., Corey et al., *J. Am. Chem. Soc.* 91:5675 (1969), Corey et al., *J. Am. Chem. Soc.* 92:2586 (1970), and Corey et al., *Tetrahedron Letters* 307 (1970).

Another synthetic route uses norbornadiene as a starting material, while still another approach involves the use of racemic bicyclo[3.2.0]hept-2-en-6-one as a starting material. This latter synthesis involves an enantioconvergent approach, such that the following two enantiomers are used, obviating the need for optical resolution:

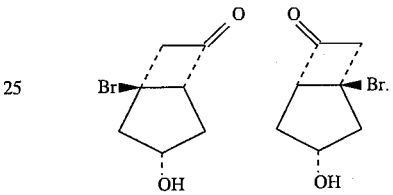

However, there remains a need in the art for a simpler and more direct route to the various prostaglandins, particularly prostaglandin $E_1$, prostaglandin $E_2$, and derivatives thereof. It is also desirable that such a synthesis provide the desired product in relatively high yield, be simple and straightforward to scale up, and involve inexpensive, commercially available reagents. The present invention is directed to such a method, and involves the use of a lithium copper reagent in a "one-pot" synthesis of $PGE_1$, $PGE_2$ and analogs thereof.

RELATED ART

In addition to the publications identified in the preceding section, the following references are also of interest as they relate to methods for synthesizing prostaglandin derivatives.

U.S. Pat. Nos. 4,031,129 and 4,088,536 to Sih relates to a method for preparing racemic 15-deoxyprostaglandin $E_1$ by reacting lithium cyclopentadiene with ethyl-7-bromoheptanoate, oxygenating the alkylated diene so provided, recovering 2-(6'-carboethoxyhexyl)-4-hydroxycyclopenten-1-one from the reaction mixture, reacting with dihydropyran to give the tetrahydropyranyl ether, and, finally, reacting that intermediate with 1-lithium-1-trans-octene in the presence of tri-n-butylphosphine-copper iodide to yield racemic 15-deoxy prostaglandin $E_1$, ethyl ester.

U.S. Pat. No. 4,149,007 to Buckler et al. relates to a method for synthesizing prostaglandin $E_1$ derivatives having a phenyl substituent at the C-14 position; the method involves the use of an organolithium cuprate reagent in order to add on the side-chain at the C-12 position. This coupling is followed by deprotection with a weak acid and hydrolysis.

U.S. Pat. No. 4,282,372 to Matsuo et al. describes a process for preparing cyclopentenolone derivatives stated to be useful as intermediates for producing, inter alia, prostaglandins. The process involves conversion of substituted furans under acidic conditions, or with chlorine or bromine in the presence of an alkali and an alcohol.

U.S. Pat. No. 4,360,688 to Floyd, Jr. relates primarily to methods for synthesizing prostaglandin derivatives in which a pendant —S-Aryl moiety is present within the side chain extending from the C-8 position. Also disclosed is a method for reacting such compounds so as to convert the ethylene moiety bearing the —S-Aryl group to a vinylene group.

U.S. Pat. No. 4,452,994 to Hill et al. relates to a method for isolating an 11,16- or 11,15-dihydroxyprostaglandin from a reaction mixture. The process involves the use of a lithium halide.

U.S. Pat. Nos. 4,474,979, 4,644,079, 4,983,753 and 5,166,369 to Floyd, Jr. et al. relates a synthetic process which involves protection of the 4-hydroxyl group of a cyclopentenyl moiety of a cyclopentenoyl compound with, e.g., a trimethylsilyl or tetrahydropyranyl group, followed by conversion to the desired prostaglandin (a 1-methyl-16, 16-dimethyl-11α, 15α-dihydroxy-9-oxo-2,13-trans,trans-prostadienoate) using a lithiocuprate reagent such as lithiocuprate-1-pentyne.

U.S. Pat. No. 4,535,180 to Grudzinskas et al. describes methods for synthesizing prostaglandin analogues are claimed. However, all of the claimed compounds have either a methyl group or a $C_2$–$C_4$ alkenyl bonded directly to the cyclopentane ring.

U.S. Pat. No. 4,543,421 to Corey et al. describes a method for adding a side chain "$R_1$" onto a prostaglandin analogue at the C-12 position. The method involves the use of an alkyllithium reagent with CuCN to form a lithium cyanocuprate; this compound is then reacted with a substituted cyclopentenone, which step is optionally followed by hydrolysis.

U.S. Pat. Nos. 4,785,124 and 4,904,820 to Campbell et al. describe preparation of higher order cuprate complexes derived from reaction of a cuprate complex with a stannane such as 1,2-bis-tri-n-butylstannyl ethylene, which are in turn used in the preparation of omega side chains of prostaglandins.

U.S. Pat. No. 4,952,710 to Babiak et al. describes preparation of cyclopenteneheptenoic acid derivatives by reacting higher order cuprate complexes with a chiral cyclopentene.

U.S. Pat. No. 5,055,604 to Babiak et al. relates to a synthesis for preparing a prostaglandin derivative which involves (1) production of an "E-alkenyl" zirconium compound by reacting an alkyne and zirconocene chloride hydride; (2) reacting that compound with a lithium cyanocuprate reagent to produce a cuprate complex intermediate; and (3) reacting the cuprate complex intermediate with a cyclopentenone.

U.S. Pat. No. 5,191,109 to Minai et al. describes a process for preparing an optically active 4-hydroxycyclopentenone. The process involves reacting a half ester (VI) with furan in the presence of trifluoroacetic acid anhydride to obtain a furfuryl ketone, later reducing to a furancarbinol. The furancarbinol is treated in an aqueous solvent at pH 3.5–6 to give a 3-hydroxycyclopentenone or racemic 4-hydroxycyclopentenone, followed by further treatment with an aliphatic carboxylic acid to give the product.

Japanese Patent Publication (Kokai) No. 63-077837 describes conversion of a substituted furan compound to cyclopentenone compounds.

Lipshutz, "Applications of Higher-Order Mixed Organocuprates to Organic Synthesis," *Synthesis* 4:325–341 (1987), presents an overview of the use of cuprate complexes to create new carbon-carbon bonds in a variety of synthetic contexts. Specifically, preparation and use of higher order cuprates complexes of formulae RtRCu(CN)Li$_2$ and RtRCu(SCN)Li$_2$ is described. "Rt" represents the group which is transferred to an organic compound to form a carbon-carbon bond, with R representing a residual group.

SUMMARY OF THE INVENTION

It is accordingly a primary object of the invention to address the above-mentioned need in the art by providing a straightforward, "one-pot" reaction to the synthesis of prostaglandins such as PGE$_1$, PGE$_2$ and derivatives thereof.

It is another object of the invention to provide such a synthesis which involves reaction of an appropriately substituted cyclopentenone with a furyl copper reagent.

It is still another object of the invention to provide such a synthesis wherein the furyl copper reagent is provided by reaction of 2-furyllithium, copper cyanide (CuCN), lower alkyllithium and either an (E)-alkenylstannane or a halogenide.

It is yet another object of the invention to provide such a synthesis wherein the reaction of the aforementioned compounds is conducted simultaneously rather than sequentially, without need to distinguish between synthetic process steps and without isolation of intermediates or the like.

Additional objects of the invention will be apparent to one skilled in the art of synthetic organic chemistry upon review of the present disclosure and claims.

In accordance with the invention, then, a process is provided for synthesizing prostaglandin E$_1$, prostaglandin E$_2$, and derivatives thereof, all of which may be generically represented by the structure of Formula (I)

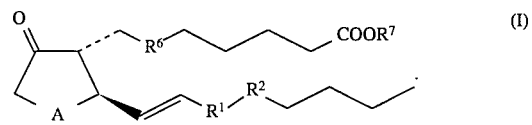

In Formula (I):

R$^1$ and R$^2$ may be the same or different and are selected from the group consisting of

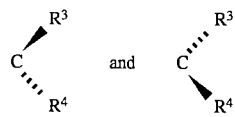

in which R$^3$ and R$^4$ are independently selected from the group consisting of hydrogen, OR$^5$ and lower alkyl;

A is selected from the group consisting of

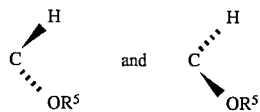

in which R$^5$ is selected from the group consisting of hydrogen, tetrahydropyranyl, tetrahydrofuranyl, triloweralkylsilyl, 1-methyl-1-methoxyethyl, 1-methyl-1-ethoxyethyl and —(CO)—R$^8$, wherein R$^8$ is hydrogen, lower alkyl, or halogen-substituted lower alkyl;

R$^6$ is ethylene or vinylene; and

R$^7$ is R$^5$, lower alkyl or lower alkenyl.

The process involves reaction of the cyclopentenone of Formula (II)

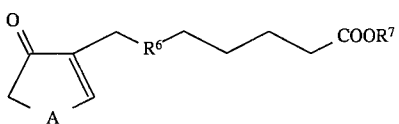

in which A, $R^6$ and $R^7$ are as defined above, with a mixture of 2-furyllithium, copper cyanide, a lower alkyllithium reagent, and either halogenide (III) or (E)-alkenylstannane (IV)

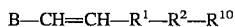

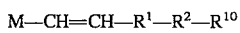

In compound (III), B is halogenide, and $R^1$ and $R_2$ are as defined above. In compound (IV), M is $-Sn(R^9)_3$ wherein $R^9$ is lower alkyl. The substituent $R^{10}$ in compounds (III) and (IV) is lower alkyl.

DETAILED DESCRIPTION OF THE INVENTION

Before describing the present invention in detail, it is to be understood that unless otherwise stated this invention is not limited to particular reagents, reaction conditions, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the content clearly dictates otherwise. Thus, for example, reference to "a cyclopentenone" includes mixtures of cyclopentenones, reference to "an alkyllithium reagent" includes mixtures of such reagents, and the like.

In this specification and in the claims which follow, reference will be made to a number of terms which shall be defined to have the following meanings:

The term "prostaglandin" as used herein refers to compounds having the prostan-1-oic acid skeleton

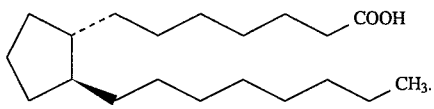

The prostaglandins prepared using the present synthesis are $PGE_1$, $PGE_2$, and derivatives thereof, i.e., compounds having the structure of Formula (I) above.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "lower alkyl" intends an alkyl group of one to eight, preferably one to six, and most preferably one to four carbon atoms. The term "halogenated lower alkyl" intends a lower alkyl group of one to six carbon atoms in which at least one hydrogen atom, typically one to three hydrogen atoms, but most typically just one hydrogen atom, is replaced with a halogen atom.

The term "alkenyl" refers to a branched or unbranched hydrocarbon chain containing from 2 to 24 carbon atoms and at least one double bond. "Lower alkenyl" refers to an alkenyl group of two to eight, more preferably two to six, and most preferably two to four, carbon atoms. The term "halogenated lower alkenyl" intends a lower alkenyl group in which at least one hydrogen atom is replaced with a halogen atom.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to eight, more preferably one to six, and most preferably one to four, carbon atoms.

"Halo," "halogen," or "halogenide" refers to fluoro, chloro, bromo or iodo, and usually relates to halo substitution for a hydrogen atom in an organic compound. Of the halos, chloro is typically preferred.

"Optional" or "optionally" means that the subsequently described circumstance may or may not occur, and that the description includes instances where said circumstance occurs and instances where it does not. For example, the phrase "optional covalent bond" means that a covalent bond may or may not be present and that the description includes both the instance when the covalent bond is present and the instance when the covalent bond is not present.

As noted above, compounds having the structure of formula (I)

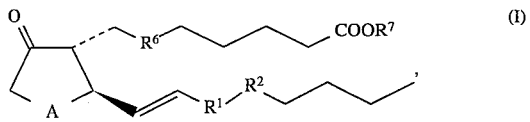

(II)

in which A, $R^1$, $R^2$, $R^6$ and $R^7$ are as defined above, are prepared by reaction of the substituted cyclopentenone

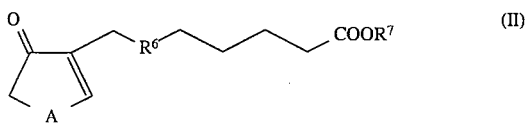

with 2-furyllithium, copper cyanide, a lower alkyllithium reagent and either halogenide (III) or (E)-alkenylstannane (IV). It is preferred that these latter four reagents be present in approximately equimolar amounts, although some variation in relative quantities, generally up to 10 to 20 mole %, can be accommodated without any significant loss in yield. The reaction is conducted in a suitable organic solvent, preferably a nonpolar, aprotic solvent such as tetrahydrofuran (THF) or diethyl ether, at a reaction temperature in the range of about –50° C. to about 50° C., preferably in the range of about –30° C. to about 30° C. The reaction should be conducted under inert conditions, i.e., under dry nitrogen or an argon gas blanket, for a reaction time of at least about thirty minutes.

Initially, it is preferred that 2-furyllithium (prepared by admixture of approximately equimolar amounts of furan and an alkyllithium reagent at a temperature of about 10° C. or lower) be combined with copper cyanide, lower alkyllithium, and either (III) or (IV) prior to addition of the cyclopentenone. The admixture of furan, the alkyllithium reagent and copper cyanide gives rise to the reagent (V)

a compound which is stable at 0° C. for relatively long periods of time, typically up to at least about six months. Addition of either (III) or (IV), followed by one-pot addition of cyclopentenone (II) to the reaction mixture, at a mole ratio in the range of about 0.3:1 to approximately 1:1 (that is, when approximately 1 mole each of furan, alkyllithium, and either (III) or (IV) are present, 0.3 to 1 mole cyclopentenone will be added), yields the desired prostaglanin derivative.

The reaction is quenched with base, e.g., ammonium hydroxide or the like. The organic materials are separated and dried (e.g., over magnesium sulfate); the product is then deprotected with, e.g., dilute hydrochloric acid, and isolated by conventional means, e.g., using chromatography, crystallization, or like techniques.

With respect to the specific reagents used, it will be appreciated by those skilled in the art of synthetic organic chemistry that reagents which are functionally equivalent to those specifically disclosed may be substituted therefor, if desired, e.g., 2-furylmagnesium chloride or bromide may be substituted for 2-furyllithium, and various lower alkyllithium reagents can be used, e.g., methyllithium, ethyllithium, isopropyllithium, n-propyllithium or the like.

Examples of preferred halogenides having the structural formula (III) include, but are not limited to, the following:

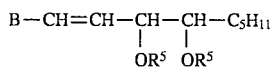

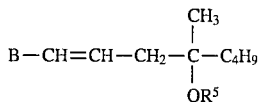

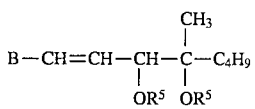

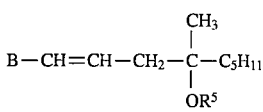

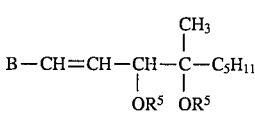

and

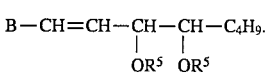

Examples of suitable (E)-alkenylstannanes include, but are not limited to, the following:

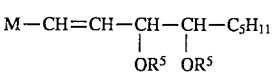

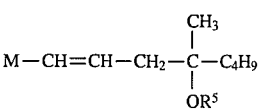

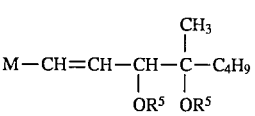

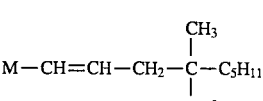

-continued

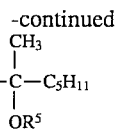

and

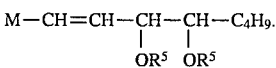

It should also be noted that if the halogenide (III) or (E)-alkenylstannane (IV) is used in enantiomerically pure form, the product may be produced in enantiomerically pure form as well. This is exemplified in the experimental section, below.

All starting materials and reagents used in the present synthesis are commercially available or may be readily synthesized using conventional techniques. For example, alkyllithium reagents, furan and copper cyanide may be obtained from a number of commercial sources, while racemic cyclopentenones of formula (II) may be prepared using the method of Collins et al., *J. Med. Chem.* 20:1152 (1970), enantiomerically pure cyclopentenones of formula (II) may be prepared using the method of Pappo et al., *Tet. Lett.*, 1973, p. 943, halogenides of formula (III) may be prepared using the methods of Jung et al., *Tet. Lett.*, 1982, p. 3851, Weis et al., *J. Org. Chem.*, 1979, p. 1438, or Collins et al., *J. Med. Chem.*, 1977, p. 1152, and alkenylstannanes of formula (IV) may be synthesized using the method of Chen et al., *J. Org. Chem.* 43:3450 (1978).

Advantages of this procedure are excellent isolable yields—in most cases over 80 to 90%—and very good reproducibility. The process is simple to scale-up and enables production of hundreds of grams of prostaglandins in a "one-pot" operation. Side products are easy to separate using conventional techniques such as crystallization or chromatographic methods, and a high purity prostaglandin product is isolated. From a manufacturing standpoint, it is advantageous that the reagent mixture is stable and when necessary can be stored for long periods of time, on the order of six months or longer, without appreciable decomposition. All process chemicals are inexpensive and commercially available.

The following examples are intended to provide those of ordinary skill in the art with a complete disclosure and description of how to conduct the present synthetic process, and are not intended to limit the scope of that which the inventors regard as their invention. Efforts have been made to insure accuracy with respect to numbers used (e.g., amounts, temperatures, etc.), but some experimental error and deviation should, of course, be allowed for. Unless indicated otherwise, parts are parts by weight, temperatures are in degrees centigrade, and pressure is at or near atmospheric.

Experimental

All organometallic reactions were performed under dry nitrogen or under an argon gas blanket using anhydrous solvents. Reaction flasks were dried with a heat gun prior to addition of starting materials or reagents and all air-sensitive reactants were transferred via cannula. Identity of products was confirmed by $^1$H and $^{13}$C NMR (using a Jeol 270 MHz spectrometer), infrared spectroscopy (using a Mattson Galaxy 5020 Series Fourier-Transform spectrometer), gas chromatography (using a Hewlett-Packard 5890 GC/MS system) and HPLC (using a Hewlett-Packard 1050 LC) and by comparison with authentic standards when available.

EXAMPLE 1

In situ formation of lithium (E)-alkenyl-2-furylcopper-cyanide complex and its conversion to misoprostol:

To copper cyanide (2.6 g, 28.9 mmol) (Aldrich) in a heat gun dried round bottom 250 ml 3 neck flask was added anhydrous THF (35 ml), followed by a solution of 2-furyllithium (1 eq.) at 0° C. The solution was treated with methyllithium (1 eq.) and R,S-stannane 1 (1.5 eq.) (synthesized according to the method of Chen et al., supra) via cannula.

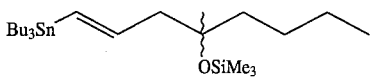

The resulting homogenous solution was stirred at ambient temperature for 3 hours, cooled to −65° C. and protected R,S-enone 2 (7 g. 19.8 mmol) (synthesized according to the method of Collins et al., supra) in THF (35 ml) was added in one portion. The temperature was observed to rise to approximately −35° C.

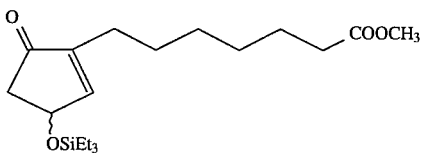

The homogenous reaction mixture was stirred at −30° C. to about −40° C. for 30 minutes and quenched with a saturated aqueous solution of ammonium chloride (500 ml, containing 50 ml conc. ammonium hydroxide) and ethyl acetate (150 ml). Organic materials were separated, dried over magnesium sulfate and evaporated in vacuum at approximately 45° C. to 55° C. to give crude R,S-methyl-13E, 11-triethylsilyloxy-16-trimethylsilyloxy-16-methyl-9-oxoprost-13-ene-1-oate, which was then deprotected with 3M HCl in acetone (30 min) to give crude misoprostol as pale yellow oil. Misoprostol was purified by chromatography on silica gel using a mixture of hexanes and methyl-t-butylether as a gradient eluant. Yield of pure misoprostol 3, 6.95 g (92%) as a colorless oil. $^1$H NMR (CDCl$_3$, ppm): 3.63 (s, OCH$_3$), 2.64 and 2.74 (dd, C-10), 5.50 (m,C-13, 14).

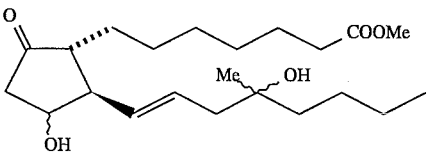

EXAMPLE 2

In situ formation of lithium (E)-alkenyl-2-furylcopper-cyanide complex and its conversion to (with n-butyllithium) misoprostol:

The procedure of Example 1 was repeated, except that a 1.6M solution of n-butyllithium in hexane (18 ml, 29 mmol) was used instead of methyllithium. Isolable yield 6.8 g (90%).

EXAMPLE 3

In situ formation of lithium (E)-alkenyl-2-furylcopper-cyanide complex and its conversion to prostaglandin E1:

The procedure of Example 1 was repeated, except that 18.6 g (35 mmol) of S-stannane 4

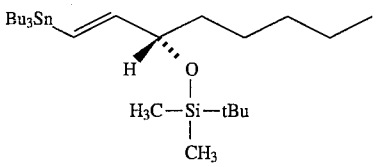

in THF (35 ml) (synthesized according to the method of Chen et al., supra) was used instead of reagent 1 and 9.5 g (21 mmol) of R-enone 5 in THF (35 ml) (synthesized according to the method of Pappo et al., supra), 1973, p. 943) was used instead of R,S-enone 3.

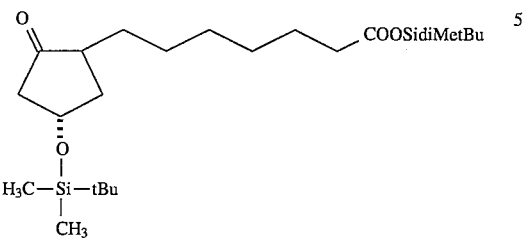

Prostaglandin E$_1$ (6.3 g; 85%) was isolated after deprotection (2M HCl-acetone 1:1, 30 min RT) and chromatography. $^1$H NMR (CDCl$_3$, ppm): 2.61 and 2.,65 (dd, 10-C) 0.90 (t, C-20).

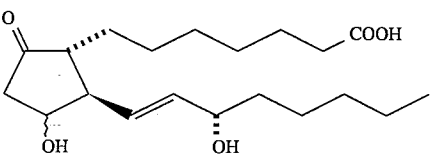

Prostaglandin E1

EXAMPLE 4

In situ formation of lithium (E)-alkenyl-2-furylcopper-cyanide complex and its conversion to prostaglandin E2:

The procedure of Example 1 was followed, using S-stannane 6 (synthesized according to the method of Chen et al., supra) in place of the R,S-stannane 1.

(wherein "THP" represents tetrahydropryanyl) and R-enone 7 (synthesized using the method of Pappo et al., supra) in place of R,S-enone 2.

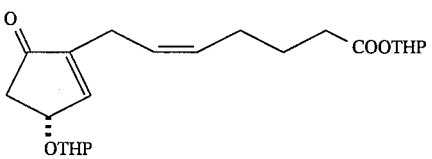

Prostaglandin E$_2$ (80%) was obtained after deprotection (2M HCl-acetone 1:1, 15 min at room temperature and chromatography.

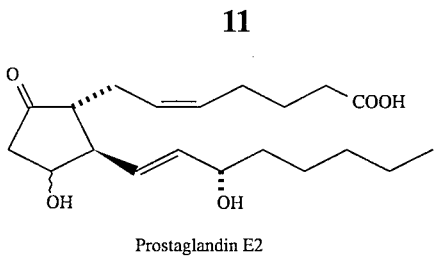

Prostaglandin E2

EXAMPLE 5

In situ formation of lithium (E)-alkenyl-2-furylcoppercyanide complex and its conversion to prostaglandin $E_1$ methyl ester:

The procedure of Example 1 was repeated, except that S-stannane 8

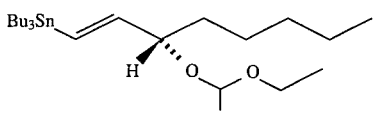

(17 g, 35 mmol) (synthesized using the method of Chen et al., supra) in THF (35 ml) was used instead of S-stannane 1 and R-enone 9 (6.55 g, 21 mmol) (synthesized according to Pappo et al., supra) in THF (35 ml) was used instead of R-enone 2.

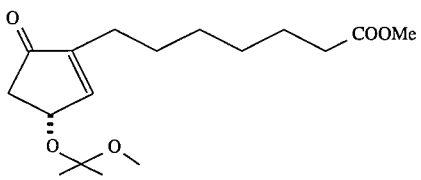

Prostaglandin $E_1$ methyl ester was obtained (6.6 g; 85%).

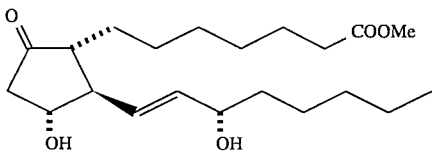

Prostaglandin E1 methyl ester

EXAMPLE 6

In situ formation of (E)-alkenyl-2-furylcopper lithium cyanide and its conversion to prostaglandin $E_1$:

To copper cyanide (2.6 g, 28.9 mmol) in a 250 ml 3 neck flask was added THF (35 ml), followed by a solution of 2-furyllithium in THF at 0° C. (prepared by treating furan with n-butyllithium in hexanes at 0° C.). The resulting solution was cooled below −65° C. and a solution of (E)-alkenyllithium (prepared from S-(E)-alkenyl iodide 10, or S-stannane 11 and n-butyllithium at −70° C. for 1 hour) was added via cannula. The resulting amber-colored mixture was stirred for 30 minutes (−60° C.) and R-enone 12 (9.54 g, 21 mmol) in THF (40 ml) was added

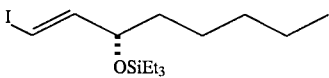

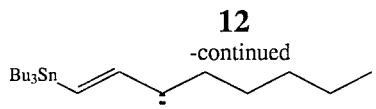

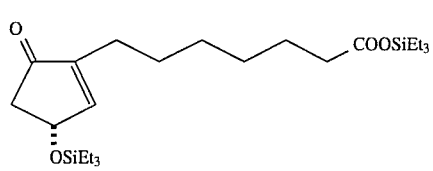

The homogenous mixture was stirred for 30 minutes at −50° C., and saturated aqueous ammonium chloride/ammonium hydroxide (10%) (500 ml) was added at once, followed by continued stirring for 1 hour at ambient temperature. The organic layer was separated, washed (2×) with brine, dried and evaporated. Crude $PGE_1$ was obtained after deprotection with 500 mg pyridinium p-toluenesulfonate in 150 ml acetone and 30 ml water for 5 hours. The product was purified by column chromatography on silica gel using ethyl acetate-hexanes 2:1 as eluant and crystallization from ether. Yield 6.6 g (89%).

We claim:

1. A process for preparing prostaglandins having the structural formula (I)

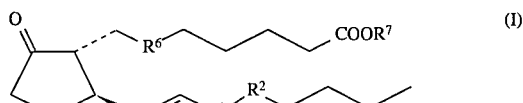

wherein $R^1$ and $R^2$ may be the same or different and are selected from the group consisting of

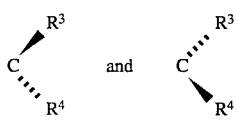

in which $R^3$ and $R^4$ are independently selected from the group consisting of hydrogen, $OR^5$ and lower alkyl, A is selected from the group consisting of

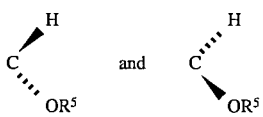

in which $R^5$ is selected from the group consisting of hydrogen, tetrahydropyranyl, tetrahydrofuranyl, triloweralkylsilyl, 1-methyl-1-methoxyethyl, 1-methyl-1-ethoxyethyl and —(CO)—$R^8$, wherein $R^8$ is hydrogen, lower alkyl or halogen-substituted lower alkyl, $R^6$ is ethylene or vinylene, $R^7$ is $R^5$, lower alkyl or lower alkenyl, which process comprises:

(a) preparing a reaction mixture containing (i) a first reagent selected from the group consisting of 2-furyllithium, 2-furylmagnesium chloride and 2-furylmagnesium bromide, (ii) a second reagent comprising a lower alkyllithium compound, (iii) a third reagent comprising copper cyanide, and (iv) a fourth reagent comprising either halogenide (III) or (E)-alkenylstannane (IV)

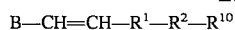  (III)

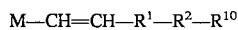  (IV)

in which B is halogenide, M is —Sn(R$^9$)$_3$ wherein R$^9$ is lower alkyl, R$^{10}$ is lower alkyl, and R$^1$ and R$^2$ are as defined above;

(b) contacting cyclopentenone (II)

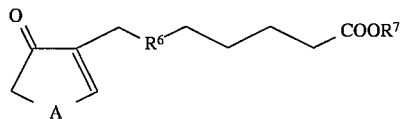  (II)

with the reaction mixture under conditions effective to give rise to one or more products having the structural formula (I).

2. The process of claim 1, wherein the first reagent is 2-furyllithium.

3. The process of claim 2, wherein the second reagent is selected from the group consisting of methyllithium, ethyllithium, n-propyllithium, isopropyllithium, n-butyllithium, isobutyllithium and t-butyllithium.

4. The process of claim 1, wherein the fourth reagent has the structural formula (III).

5. The process of claim 2, wherein the fourth reagent has the structural formula (III).

6. The process of claim 5, wherein the fourth reagent is selected from the group consisting of

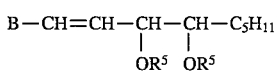

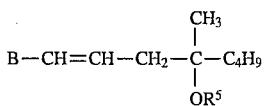

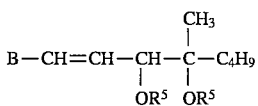

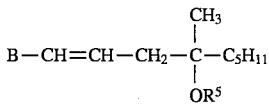

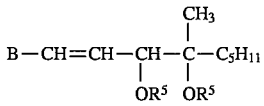

and

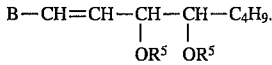

7. The process of claim 1, wherein the fourth reagent has the structural formula (IV).

8. The process of claim 2, wherein the fourth reagent has the structural formula (IV).

9. The process of claim 8, wherein the fourth reagent is selected from the group consisting of

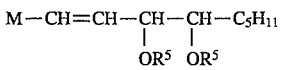

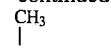

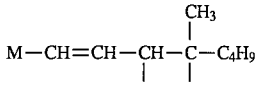

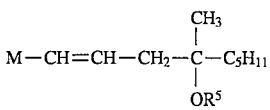

and

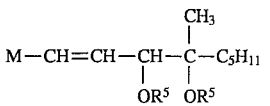

10. The process of claim 1, wherein the first, second, third and fourth reagents are present in the reaction mixture in approximately equimolar quantities.

11. The process of claim 1, wherein the mole ratio of cyclopentenone (II) to any one of the first, second, third or fourth reagents is in the range of approximately 0.3:1 to 1:1.

12. The process of claim 1, wherein the product is obtained without isolation of any intermediate species.

13. The process of claim 1, wherein step (b) is conducted in a nonpolar, aprotic solvent at a reaction temperature in the range of approximately –50° C. to 50° C. for at least about thirty minutes.

14. The process of claim 10, wherein step (b) is conducted in a nonpolar, aprotic solvent at a reaction temperature in the range of approximately –50° C. to 50° C. for at least about thirty minutes.

15. The process of claim 1, further including (c) quenching the reaction of step (b) with base.

16. The process of claim 15, further including (d) deprotecting the product of step (c) with dilute acid, and (e) isolating the product (I) using chromatography or crystallization.

17. A process for preparing prostaglandins having the structural formula (I)

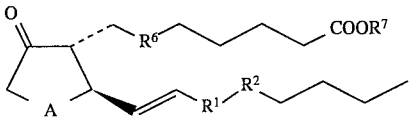  (I)

wherein

R$^1$ and R$^2$ may be the same or different and are selected from the group consisting of

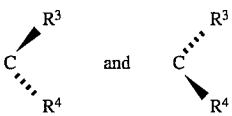

in which R$^3$ and R$^4$ are independently selected from the group consisting of hydrogen, OR$^5$ and lower alkyl, A is selected from the group consisting of

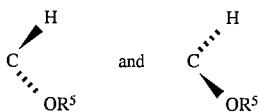

in which $R^5$ is selected from the group consisting of H, tetrahydropyranyl, tetrahydrofuranyl, triloweralkylsilyl, 1-methyl-1-methoxyethyl, 1-methyl-1-ethoxyethyl and —(CO)—$R^8$, wherein $R^8$ is hydrogen, lower alkyl or halogenated lower alkyl, $R^6$ is ethylene or vinylene, $R^7$ is $R^5$ lower alkyl or lower alkenyl, which process comprises:

(a) preparing a reaction mixture containing approximately equimolar amounts of (i) 2-furyllithium, (ii) a lower alkyllithium compound, (iii) copper cyanide, and (iv) either halogenide (III) or (E)-alkenylstannane (IV)

in which B is halogenide, M is —Sn($R^9$)$_3$ wherein $R^9$ is lower alkyl, and $R^1$ and $R^2$ are as defined above;

(b) contacting cyclopentenone (II)

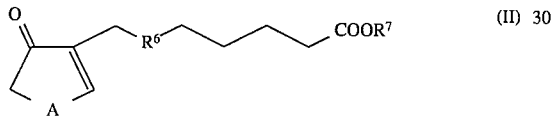

with the reaction mixture in a nonpolar, aprotic solvent at a reaction temperature in the range of approximately −50° C. to 50° C. for at least about thirty minutes, without isolation of any intermediate species;

(c) quenching the reaction of step (b) with base;

(d) deprotecting the product of step (c) with dilute acid; and (e) isolating the product (I) using chromatography or crystallization.

18. The process of claim 1, wherein $R^6$ is ethylene.

19. The process of claim 18, wherein compound (I) is prostaglandin $E_1$.

20. The process of claim 18, wherein compound (I) is Misoprostol.

21. The process of claim 1, wherein $R^6$ is vinylene.

22. The process of claim 21, wherein compound (I) is prostaglandin $E_2$.

23. The process of claim 17, wherein $R^6$ is ethylene.

24. The process of claim 23, wherein compound (I) is prostaglandin $E_1$.

25. The process of claim 23, wherein compound (I) is Misoprostol.

26. The process of claim 17, wherein $R^6$ is vinylene.

27. The process of claim 26, wherein compound (I) is prostaglandin $E_2$.

* * * * *